United States Patent [19]

Wehling

[11] Patent Number: 5,279,825

[45] Date of Patent: Jan. 18, 1994

[54] METHOD OF ENHANCING THE REGENERATION OF INJURED NERVES AND ADHESIVE PHARMACEUTICAL FORMULATION THEREFOR

[75] Inventor: Peter Wehling, Monheim, Fed. Rep. of Germany

[73] Assignee: Advance Biofactures of Curacao, N.V., Curacao, Netherlands Antilles

[21] Appl. No.: 941,570

[22] Filed: Sep. 8, 1992

Related U.S. Application Data

[62] Division of Ser. No. 593,778, Oct. 5, 1990, Pat. No. 5,173,295.

[51] Int. Cl.$^5$ ............................................. A61K 37/54
[52] U.S. Cl. ................................. 424/94.67; 424/530; 514/2; 514/21
[58] Field of Search ................. 424/94.67, 530; 514/2, 514/21

[56] References Cited

U.S. PATENT DOCUMENTS 4,983,393 1/1991 Cohen et al. .......................... 424/484
5,045,601 9/1991 Capelli et al. ....................... 525/327.1

OTHER PUBLICATIONS

Copelas et al., Pflugers Arch 408(3):315-317 (1987).

Primary Examiner—Douglas W. Robinson
Assistant Examiner—Jean C. Witz
Attorney, Agent, or Firm—Roland Plottel

[57] ABSTRACT

The regeneration of injured nerves is enhanced by supplying collagenase to the zone of injury of the nerve. Growth of nerve sprouts over the zone of injury is aided by the presence of effective amounts of collagenase during the regeneration process. If the nerve has been severed, collagenase is supplied to the ends of the proximal and distal stumps. A nerve graft may be interposed between the stumps. Natural fibrin has been used as glue to join nerve stumps, and collagenase is effective when used in admixture with fibrin.

6 Claims, 5 Drawing Sheets

METHOD OF ENHANCING THE REGENERATION OF INJURED NERVES AND ADHESIVE PHARMACEUTICAL FORMULATION THEREFOR

This application is a division, of application Ser. No. 07/593,778, filed Oct. 5, 1990, now U.S. Pat. No. 5,173,295.

BACKGROUND

Considerable success has been achieved in recent years in the repair of injured nerves, including those wherein complete severance of a nerve trunk has occurred. Microsurgery has enhanced the ability to match nerve ends precisely, but itself introduces additional trauma. Success of nerve repair is uncertain at best, not only because of surgical difficulties but also because of the many interrelated biological events occurring at the site of injury and beyond the site of injury.

Functional recovery after nerve repair is dependent on structural and functional events in the peripheral as well as the central nervous system. The pattern of cellular and biochemical events required to achieve useful sensory and motor regeneration after a nerve injury is complex. Among necessary factors are survival of the nerve cell body, initiation of the sprouting process, growth of sprouts over the zone of injury, reinnervation of endoneurial tubes in the distal segment, reinnervation of peripheral targets and maturation of nerve fibers/target structures.

Some of these problems can be approached surgically. The surgeon can influence the result by the way he or she handles the damaged nerve and by the method chosen for reconstruction. Other factors susceptible to influence are the timing of surgery and postoperative reeducation and rehabilitation. At present the remaining components of the regeneration process are more or less out of reach, but some may prove to be critical factors to address in the future.

SUMMARY OF THE INVENTION

The present invention deals with problems surrounding growth of nerve sprouts over the zone of injury, whether the injury results in total severance of a nerve trunk, or the condition known as "neuroma in continuity" where damage is caused by crushing; bruising, or partial laceration of the nerve.

In accordance with this invention, regeneration of injured nerves is enhanced by supplying an effective amount of collagenase to the zone of injury of the nerve during the regeneration process. In one embodiment, collagenase is mixed with fibrin, which is then used as a glue between severed nerve ends. In another embodiment, a pharmaceutical kit is made up containing fibrin and collagenase, either premixed, or separate for mixing at time of surgery. The invention is useful when the stubs of severed nerves are to be reunited either directly or by interposition of a nerve graft.

CLINICAL ASPECTS OF NERVE REPAIR

In order to facilitate understanding of the intricacies of nerve surgery and the factors that affect nerve regeneration, the following discussion is provided.

Terminology

There are certain accepted surgical anatomical terminologies covering basic patterns of intraneural structures of importance for the surgical procedure. Nerve trunks have been defined as monofascicular (cross-section consists of one large fascicle), oligofascicular (cross-section consists of a few fascicles) and polyfascicular (the nerve consists of many smaller fascicles) (Millesi & Terzis, 1984). A fascicle is a small bundle of nerve fibers. The perineurium is the connective-tissue sheath that surrounds a fascicle. The epineurium is the external connective-tissue sheath of a nerve trunk. Connective-tissue contains collagen as a major component.

Role of Collagen

Although several types of collagen form part of the peripheral nerve (Pleasure, 1984; Thomas & Olsson, 1984), their role in the functional process of nerve conduction is unknown. Collagen occurs at two locations in peripheral nerve, the endoneurium and the perineurium. The collagen at each site is different (Thomas, 1963; Thomas & Olsson, 1984). It is known that the collagen content of peripheral nerve increases after complete transection of the nerve (Holmes & Young, 1942; Millest, 1977; Sunderland, 1968). Furthermore, the deposition of collagen in the gap between the cut ends of the nerve prevents axonal sprouting, regrowth and rejoining (Millesi, 1977; Pleasure et al., 1974). Millesi (1977) suggests that scar formation proceeds from the epineurium. He therefore recommends stripping the epineurium to reduce this process. However, recent studies (Eather et al., 1986) show that transection of the ischiadic nerve in rats leads to increases in collagen concentration 2.5 mm proximal and distal to the injury. This indicates that the region around the transection is involved in the process of collagen production. Thus, the production of collagen may have negative effects, but also serves essential functions in the rebuilding and regeneration of injured nerves.

The consequences of introducing collagenase into the biologically active zone of regeneration cannot be judged a priori. It has been suggested (Pinnell, U.S. Pat. Nos. 4,524,065 and 4,645,668) that mammalian scars (which contain large amounts of collagen) be prevented by administering collagenase directly into the affected area during the healing process, or be dissolved by administering directly into the lesion. Pinnell states that purified collagenase has been demonstrated to be relatively safe even in large doses in contact with human blood vessels, nerves and bones (presumably Pinnell refers to intact nerves), but there is no suggestion that it be used in the repair of injured nerves or that it would enhance nerve regeneration. It may be postulated that in the present invention one function of collagenase when supplied to the site of a nerve trauma may be to break down collagen as it is formed or after it has formed, but it is not apparent that this is the actual mechanism, or whether a favorable effect should outweigh an unfavorable effect, or whether collagenase is providing or contributing to other functions that result in overall enhancement of nerve regeneration. As stated earlier, the pattern of cellular and biochemical events required to achieve useful sensory and motor regeneration after a nerve injury is complex.

Timing

Discussions of primary versus secondary nerve repair are often based upon the time course of metabolic changes in the nerve cell body following nerve injury: after nerve transection the nerve cell body is believed to present an optimal metabolic potential 2-3 weeks following the injury (Ducker, 1980; Ducker et al., 1969) and we know that a "conditioning lesion" preceding a second lesion might help to increase the outgrowth rate of axons considerably. In addition, structural and functional changes in the distal nerve segment following transection may create optimal conditions for regeneration a couple of weeks following the initial trauma. These facts, together with clinical experience of nerve injuries seen in the Second World War (for reviews see Omer & Spinner, 1980), may form a theoretical base for recommending delayed primary repair. However, one has to keep in mind that nerve injuries seen in war are quite different from the civilian injuries usually seen in our hospitals. War injuries usually involve considerable soft tissue trauma which makes it impossible to carry out nerve surgery before the surrounding tissues have healed, the inflammatory reaction has declined and demarcation of the ultimate level of nerve injury is clear. The nature of the wound rather than aspects of nerve cell body metabolism might have been the true reason for recommending secondary nerve repair in such instances (Ducker, 1981).

Crushing and laceration of nerve trunks are sometimes seen in civilian accidents too. In these cases, the nerve should be repaired secondarily when the demarcation of the nerve injury is obvious and adequate levels for scars/neuroma excision can be defined. However, in sharp, clean-cut nerve injuries there are good reasons to recommend primary nerve repair. In the initial stage an exact orientation of the cut nerve ends is usually possible to achieve by the help of local landmarks like epineural vessels and a well-preserved fascicular pattern in the cut face of the nerve. At this stage the ends can still be sutured without tension. At a later stage, on the other hand, both the nerve segments have retracted and a great deal of scar tissue usually has to be resected (cut out). Tension at the suture line is difficult or impossible to avoid, and often a nerve graft has to be interposed.

Thus, considering the total situation, the ideal nerve suture is carried out as a primary procedure, a suggestion which is supported by experimental and clinical data (Grabb, 1968; Grabb et al., 1970; Muller & Grubel, 1981). With increasing preoperative delay the results could be expected to become progressively worse, and particularly liable to be affected by shrinkage and fibrosis of the distal nerve segment as well as degeneration of end organs.

Following nerve transection the corresponding muscles atrophy rapidly and after 2 years muscle fibers may fragment and disintegrate. If reinnervation of the muscle occurs after one year; function can at best be poor, while a delay of 18-24 months causes irreversible changes in the muscle cells with no hope for return of motor function at the time of regeneration (Wilgis, 1982). Sensory organs seem to be more resistant to denervation than muscles and the final extent of sensory recovery has been reported to have little correlation with the time of injury to nerve repair (Onne, 1962).

Techniques for Nerve Repair

The choice of technique for nerve repair has been the subject of a great deal of debate in the literature. With the introduction of microsurgical techniques, it became possible to dissect, identify, map and even suture in a selective way, individual fascicular components of nerve trunk. Since axonal misdirection at the suture line is a principal problem, there was great hope that microsurgical techniques would improve the results. However, the tissue trauma associated with resection of the epineurium and extensive interneural dissections might per se induce microhemorrhages, oedema and fibrosis, interfering with axonal growth. The mechanical advantage of exact matching of fascicular structures has therefore to be balanced against possible harmful effects of the microsurgical trauma as such.

The purpose of all nerve repair techniques is to restore continuity of the nerve trunk, including all its elements, in order to achieve optimal reinnervation of the end organs. According to Millesi and Terzis (1984). the four basic steps of nerve repair can be defined as:

1. Preparation of the stumps, often involving resection or interfascicular dissection with separation of individual fascicles or groups of fascicles.
2. Approximation, with special reference to the length of the gap between the stumps as well as the amount of tension present.
3. Co-aptation of the nerve stumps. Co-aptation describes the opposition of corresponding nerve ends with special attention to bringing the cross-section of the fascicles into optimal contact. A direct co-aptation (neurorrhaphy) can oppose stump to stump, fascicle to fascicle, or fascicle group to fascicle group in the corresponding ends. An indirect co-aptation can be performed by interposing a nerve graft.
4. Maintenance of co-aptation, involving the use of, for example, stitches glue or a natural fibrin clot as glue.

Epineural Repair

Co-aptation of the nerve stumps by suturing the external epineurium is a classic method of nerve repair (Zachary & Holmes, 1946; Zachary, 1954; Edshage, 1964; Moberg, 1964; Braun, 1980; Snyder, 1981; Wilgis, 1982). An important step is the initial debridement of the nerve edges, which can be carried out by the use of soft membranous material wrapped circumferentially around the nerve to make the end firm enough to be cut with a scalpel or a pair of scissors. Cooling of the end has been used clinically (Edshage & Niebauer, 1966) and experimentally (de Medinaceli et al., 1983) to ensure sharp resection surfaces and facilitate the co-aptation. If the nerve has been sharply cut by the damage (glass, knife), there is usually no reason for further debridement before the repair is performed. The cut surface of the nerve may show protrusion of fascicular contents; if not too extensive, this should be accepted in order to avoid further trauma. Landmarks such as longitudinal epineural blood vessels are identified to ensure a correct rotation of the nerve stumps, and the fascicular pattern of the cut ends should be identified under high magnification, to further ensure correct matching of the ends when the suture is performed. The sutures are placed circumferentially in the epineurium of both stumps, initially at points where external landmarks make the correct rotation crystal clear. Further stitches are then placed around the circumference to secure and maintain the initial orientation. Due to postoperative edema, the nerve ends swell considerably during the first few days, and if the sutures are too tight the ends will be strangulated. It is therefore important to make the sutures very loose. The number of sutures should be as few as possible, and no more than are needed to hold the ends close enough together with sufficient strength.

The advantage of the epineural suture technique is its simplicity and the minimal dissection trauma required. However, the technique does not ensure an absolutely correct matching of the fascicular structures over the nerve trunk. It was demonstrated by Edshage (1964) that the epineural suture technique may cause misalignment and considerable displacement of fascicles in spite of a perfect superficial appearance of the epineural adaptation.

Fascicular Repair

The object of fascicular repair, or more correctly "group fascicular repair" is to achieve an optimal orientation by approximating and adapting fascicles or groups of fascicles individually (Sunderland, 1981; Kurze, 1964; Smith, 1964; Bora, 1967; Hakstian, 1968; Grabb et al., 1970; Millest, 1973; Cabaud et al., 1976, 1980; Ito et al., 1976; van Beek & Kleinert, 1977; Terzis & Strauch, 1978; Lilla et al., 1979; Terzis, 1979; Tupper, 1980; Kline et al., 1981; Kutz et al., 1981). Fascicular groups are carefully freed by dissection under high magnification, and the epineural tissue is resected over a short distance from the cut nerve.

Corresponding fascicular structures in both cut nerve ends should be inspected under high magnification, and co-aptation with exact matching of the fascicular groups is accomplished by placing 9-0 or 10-0 sutures in the interfascicular epineurium. Co-aptation by placing suture material in the perineurial sheath of individual fascicles is associated with extensive dissection trauma and makes sense only in nerves with few fascicles. The risk of damaging fascicles should be realized. Sutures penetrating the perineurium might induce microherniation of endoneurial contents and may delay restoration of an optimal endoneurial environment.

With the introduction of microsurgical techniques, the fascicular repair technique became popular, and vast clinical experience has now been gained. The repair does not resist much tension, and can therefore usually be carried out only as a primary procedure when no resection is required. Its advantage is the possibility of achieving an optimal matching of corresponding fascicular components. Resection of epineural tissue serves to remove the most reactive connective tissue of the nerve and can facilitate the fascicular matching. However, resection of epineurium combined with separation of fascicular groups may induce considerable tissue trauma; including vascular injury and postoperative edema. The method has therefore the potential disadvantage of surgical trauma added to the original injury. Fascicular repair requires optical magnification and can be carried out only by a skilled and experienced microsurgeon.

Nerve Grafting

Direct suture of the ends of a severed or lacerated nerve is not always possible to perform. When a nerve transection is treated secondarily, it is normally necessary to resect a scarred area around the site of a lesion in order to achieve fresh resection surfaces. After this is done, the nerve ends cannot always be brought together without considerable tension. Advanced lesions, including damage to a segment of a nerve, may result in a gap in the continuity of the nerve trunk.

Although tension can to some extent be overcome by mobilization of the nerve ends and flexion of adjacent joints, it has become apparent over recent years that tension at a suture line is disadvantageous for axonal growth. Even a slight tension can interfere with intraneural microvascular flow, compromising the nutrition of cellular components in both nerve ends. It has also been demonstrated that tension at the suture line increases scar tissue formation and decreases the quality of axonal regeneration (Millest et al., 1972a; 1976; Samii & Wallenberg, 1972; Orgel & Terzis, 1977; Miyamoto & Tsuge, 1981 a; b; Millest & Meissl, 1981). Tension reduces the transsectional area of the fascicles, thereby increasing normal endoneurial fluid pressure. On the other hand, minimal tension is not necessarily disadvantageous to axonal growth since such directed mechanical "microforces" might help to create longitudinal polarization of the fibrin clot occurring between two cut nerve ends, thus providing contact guidance for the advancing sprouts. In chamber experiments where a gap is left between the nerve ends, contractile forces in the fibrin clot contribute to the creation of a longitudinally-oriented stroma guiding axons growing toward the distal nerve segment.

Since experimental and clinical experience show that too much tension at the suture line is disadvantageous for axonal regrowth, most authors today prefer to avoid tension by bridging the gap with nerve grafts. Although this procedure has created new opportunities to achieve functionally good results even in severe nerve injuries (Millest, 1977, 1980y 1984; Millest et al., 1972b, 1976; Wilgis, 1982), not all authors agree on the critical length of the defect which should indicate the use of a nerve graft. At a panel discussion on this subject (Millesi, 1977). the opinions varied from 1.5 to 2 cm (Brunelli, Freilinger, Samii, Buck-Gramcko) to 4 mm (Kutz & Wilgis) and 6-7 cm (Urbaniak & Gaul).

Regeneration through nerve grafts has been studied experimentally in rabbits (Hudson et al., 1972) and rats (Miyamoto et al., 1981; Lundborg et al., 1982; MacKinnon, 1986). Extensive compartmentation has been observed at both the proximal and distal anastamoses (Hudson et al., 1972) and along the body of the graft (MacKinnon, 1986). Extrafascicular fibers have been observed growing in the epineurium of the graft along its whole length (4 cm in rats) (MacKinnon, 1986). although fiber counts suggested that these fibers never made functional connections. By 4 to 6 months postoperatively, the total number of fibers in the proximal segment had become constant, while there was still an increased number of smaller diameter fibers in the graft and distal segments. More fibers were present in the graft than in the distal segment indicating axonal branching at the first suture line and actual loss of fibers at the second suture line. No correlation was found between length of graft (rat peroneal nerve—length up to 2.5 cm) and number/maturation of regenerating fibers (Miyamoto et al., 1981).

Survival of Graft

The purpose of introducing grafts between the two ends of a cut nerve is to offer mechanical guidelines as well as an optimal environment for the advancing sprouts. In this respects the Schwann cells of the grafts and their basal laminae play an essential role. Laminin, located in the basal lamina of Schwann cells, is known to promote neurite growth and there are reasons to believe that certain proteins synthesized by the Schwann cells exert a neuronotrophic effect. If a thin nerve graft is placed in a healthy well vascularized bed, it will survive and will be able to fulfill this purpose. It has been demonstrated by isotope techniques that most transplanted Schwann cells in such a situation survive, multiply, form Bungner bands and remain confined to the grafted segment (Aguayo et al., 1976a, b, 1979; Charron et al., 1976; Aguayo & Bray, 1980; Aguayo, 1981). During the first day the graft survives by diffusion from the surrounding tissues. It is then revascularized rapidly, starting on the third postoperative day (Almgren, 1974). Thicker grafts have difficulties in surviving because of longer diffusion distances and delayed revascularization. The so-called "trunk graft" used in the past (for historical review, see Wilgis, 1982) usually showed a central necrosis because of its thickness.

Interfascicular Nerve Grafts

Millesi and his colleagues have shown that a gap in continuity in a nerve trunk is best treated with interfascicular nerve grafts performed with the aid of microsurgical techniques (Millest et al., 1972b, 1976). The technical details of this procedure have been described in many excellent reviews (Millesi et al., 1972a, 1976; Millesi, 1977v 1980, 1981a, b. 1984; Wilgis, 1982). It is usually performed as a secondary procedure at a time when both the retracted nerve ends may be united by abandoned scar formations. Briefly, the dissection procedure is performed from normal to abnormal tissues. The epineurium is incised to make possible the identification of groups of fascicles. Separate groups are dissected free and traced towards the site of injury. At the point where the fascicles lose their normal appearance and run into the neuroma, the group is transsected. The epineurium is excised over a distance of 1-1.5 cm from the resection borders. In order to avoid a circumferential scar; each fascicular group should be transsected at a different level.

The transsectional surfaces are studied under high magnification, and the patterns are mapped in order to identify corresponding fascicular groups. This process may be associated with considerable problems since the fascicular pattern of a nerve changes continuously along the medial course of the nerve. Moreover, the fasicular pattern of the graft does not correspond to the fascicular pattern of the nerve ends.

In nerves with fascicles arranged in groups, corresponding fascicle groups should be united by individual nerve grafts (interfascicular nerve grafts). In polyfascicular nerves without group arrangement, the fascicles may be distributed diffusely over the cross-sectional area, an arrangement which is particularly common proximally at the root level or the brachial plexus. In such cases, each sector of the cross-section should be covered by a nerve graft until the whole cross-section is complete, so-called sectoral nerve grafting (Millesi, 1980).

Source of Nerve Graft

The most common choice is the sural nerve, which has an appropriate thickness and which can be harvested in considerable lengths from both lower limbs. The sural nerve has a varying pattern ranging from monofascicular to polyfascicular, and only a few branches (Millesi, 1981b). other suitable choices are the lateral or medial antebrachial cutaneous nerves (McFarlane & Myers, 1976). The terminal parts of the posterior interosseous nerves have been used as a graft in terminal lesion of digital nerves (Wilgis & Maxwell, 1979). In rarer instances, the superficial radial or lateral femoral cutaneous nerves can be used. The graft should be reserved to avoid loss of axons through branchings (Ansselin & Davey, 1986).

According to the concept of grafting, no tension at all should be tolerated at the suture lines between the graft and host nerves. The aptation could therefore be maintained by only one or two stitches of very tiny suture material (e.g., 10-0 nylon) and even fibrin clotting may be sufficient to maintain the co-aptation if tension is completely avoided (Millesi, 1980; Futami et al., 1983; Kuderna, 1985).

A problem can sometimes occur at the distal suture line where scar formation may present an obstacle to the advance of the axonal sprouts.

Free Vascularized Nerve Grafts

It is known from experimental studies that single segmental extrinsic vessels approaching a nerve trunk can maintain the intrinsic microcirculation in the nerve over long distances. It is tempting to apply this to microvascular techniques and insert free vascularized nerve grafts in gaps in nerve continuity: if the recipient bed is heavily scarred, a conventional non-vascularized nerve graft may not be optimally vascularized. In experiments on rats, the number and average diameter of regenerating axons has been found to be greater in vascularized nerve grafts than in free non-vascularized grafts (Koshima & Harii, 1981), and regenerating axons have been reported to grow at considerably greater speed in vascularized nerve grafts than in free nerve grafts (Koshima et al., 1981).

The concept of vascularized nerve grafts was introduced by Taylor and Ham (1976) and the technique has more recently been described by, among others, Breidenbach and Terzis (1984, 1987), Boney et al. (1984). and Gilbert (1984). Five cases of segmental vascularized nerve grafts bridging scarred beds for digital sensory nerve reconstruction where previous non-vascularized nerve grafts had failed were reported by Rose and Kowalski (1985). They reported good recovery of sensibility, including average static two-point discrimination of around 9 mm.

Because of the expense, time and technical expertise required, vascularized nerve grafts must be reserved for very special occasions, primarily cases where normal revascularization of the grafts cannot be expected to take place. Among other possible advantages of vascularized nerve grafts used in a scarred recipient bed might be their ability to act as vascular carriers of non-vascularized nerve graft (Breidenbach & Terzis, 1984).

Nerve Lesion in Continuity

Peripheral nerve lesions with preserved continuity of the nerve trunk but loss of distal function to varying extents constitute one of the greatest challenges in peripheral nerve surgery. Such partial loss of function might result from subtotal nerve transsections, blunt nerve trauma or traction injuries. Various fiber components of the nerve trunk can, in such cases, present all stages from simple neurapraxia (Sunderland grade 1) to neurotmesis (Sunderland grades 3-5). While some axons may be transsected or ruptured, others may be compressed by interneural scar or compromised by vascular insufficiency. The approach to this type of injury, also called "neuroma in continuity" is extremely difficult. In these cases the surgeon may supply collagenase to the zone of injury, in accordance with the present invention. Surgical exploration, including neurolysis or resection and reconstruction, might also be indicated if the permanent situation cannot be accepted. In such cases, applying collagenase at the point of surgical intervention facilitates nerve regeneration.

The surgeon, if experienced with the type of lesion, may by inspection under high magnification be able to gauge to some extent which fascicles are healthy and should be spared and which are damaged and should be resected and replaced. However, with this method the findings can often be misleading and methods for intraoperative assessment of fiber function with electrophysiological recording techniques have been developed. Kline et al. (1968, 19691 1972) introduced techniques for intraoperative neurophysiological assessment of the extent of the lesion by stimulating and recording from whole nerves. With the development of microsurgical techniques, more refined methods for stimulation and recording from individual fascicles or fascicular groups became available. Hakstian (1968) introduced a method of stimulating motor and sensory fascicles separately in the proximal and distal nerve segments to improve accuracy in experimental nerve suture, and similar techniques have long been utilized to assess the quality of nerve regeneration following various types of nerve repair (Terzis et al., 1975, 1976; Terzis & Williams, 1976).

On the basis of these investigations, single fascicular recordings have been successfully used as an intraoperative diagnostic tool in microsurgical repair of nerve lesions in continuity (Kline & Nulsen, 1972; Williams & Terzis, 1976; Kline, 1980; Terzis et al., 1980). According to these principles, single fascicles or, if that is not possible, groups of fascicles are freed by dissection and isolated proximal and distal to the lesion. Each individual fascicle is lifted onto stimulating and recording electrodes, electrical stimuli are delivered proximally and a nerve compound, action potential (CAP) is recorded distally to the lesion. On the basis of the conduction velocity as well as the shape and amplitude of the wave form, the degree of nerve injury can be assessed and a decision made regarding the treatment of the fascicle. If there is a measurable response, intraneural neurolysis might be justified while absence of any response might indicate resection and grafting of the damaged fascicle.

Hentz et al. (1966) introduced a new principle for intraoperative recording of the small magnetic field induced by the passage of a compound action potential along a nerve. He demonstrated experimentally that virtually all parameters of the magnetic signals recorded correlated closely with the clinically useful parameters of the standard recorded CAP, and that the recording could be made without removing the nerve from its normal physiological environment, since suspension on electrodes in air is not required.

Treatment of nerve lesions in continuity must be determined in the first place by clinical examination as well as inspection and palpation of the damaged part of the nerve in situ. However, combinations of whole nerve and single fascicular recordings might, if adequate equipment and expertise are available, contribute to a correct ultimate judgment of the lesion.

DRAWINGS

The drawings show results of tests of the effect of collagenase in the regeneration of severed nerves in groups of test animals (rats)1 as compared with controls.

FIG. I shows motor performance.

FIG. II shows amplitudes of evoked muscle potential.

FIG. III shows for a single rat representative traces of evoked spinal potential and of evoked muscle potential.

FIG. IV shows velocities of motor nerve conduction.

FIG. V presents photomicrographs of nerve cross-sections.

FIG. VI shows total number of myelinized nerve fibers.

DETAILED DESCRIPTION OF THE INVENTION

Figure 1:
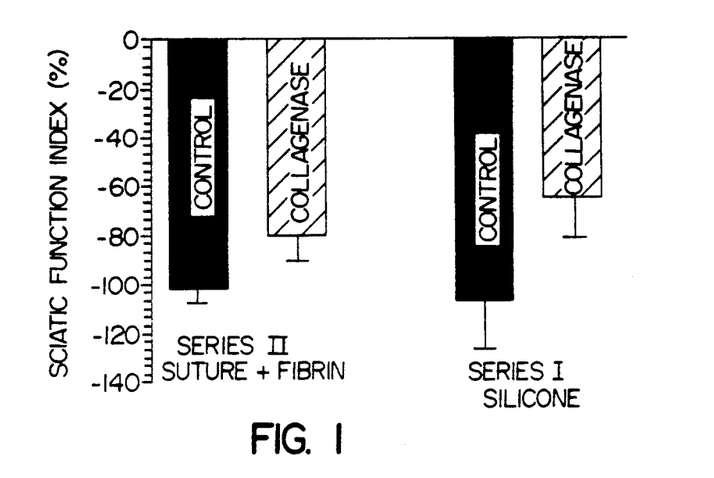
Figure 2:
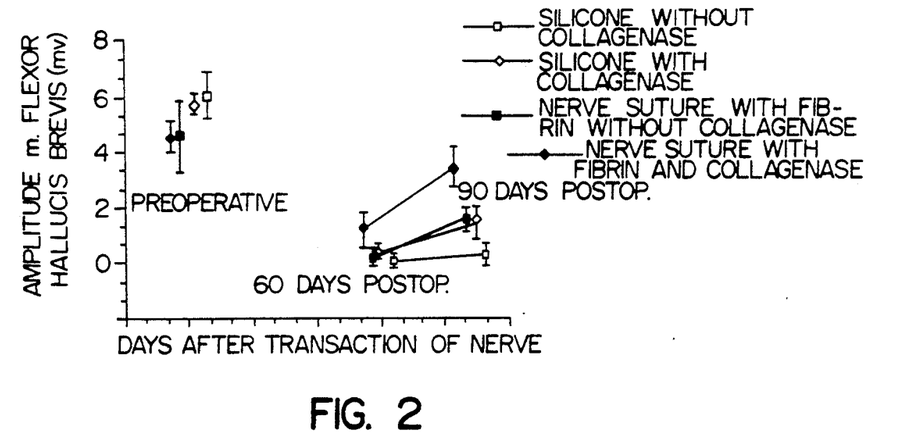
Figure 3A:
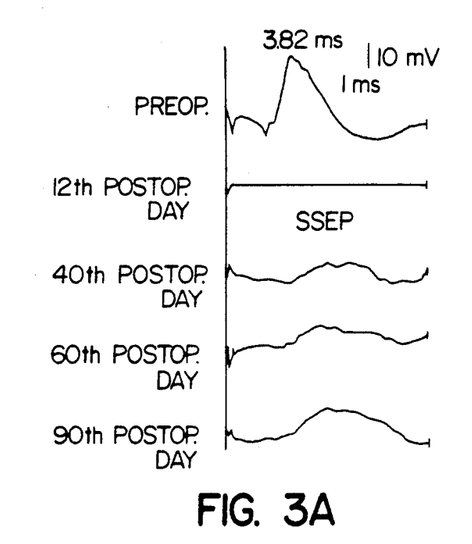
Figure 3B:
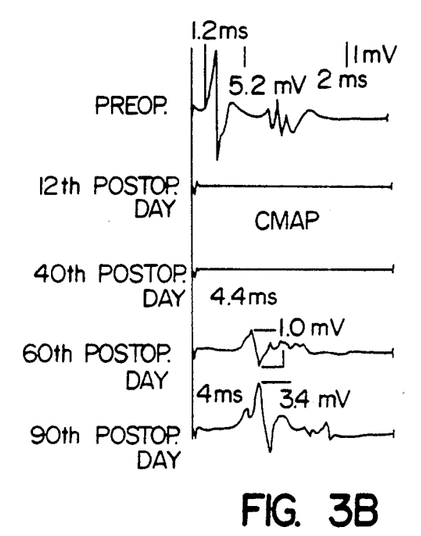
Figure 4:
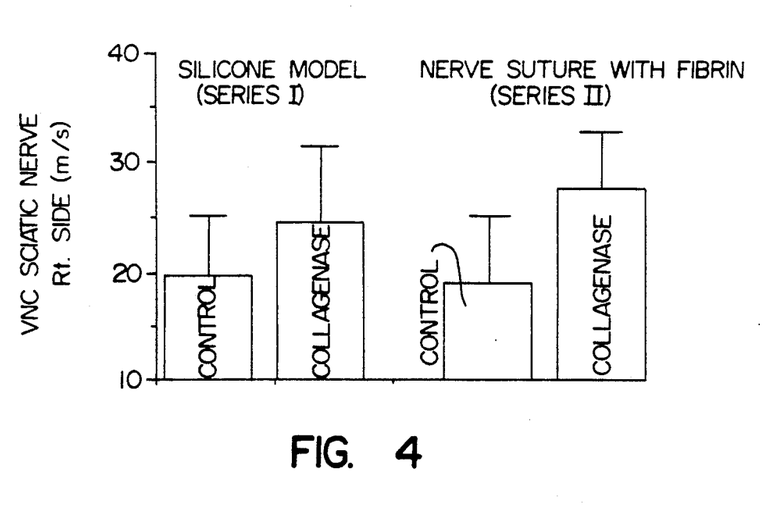
Figure 5A:
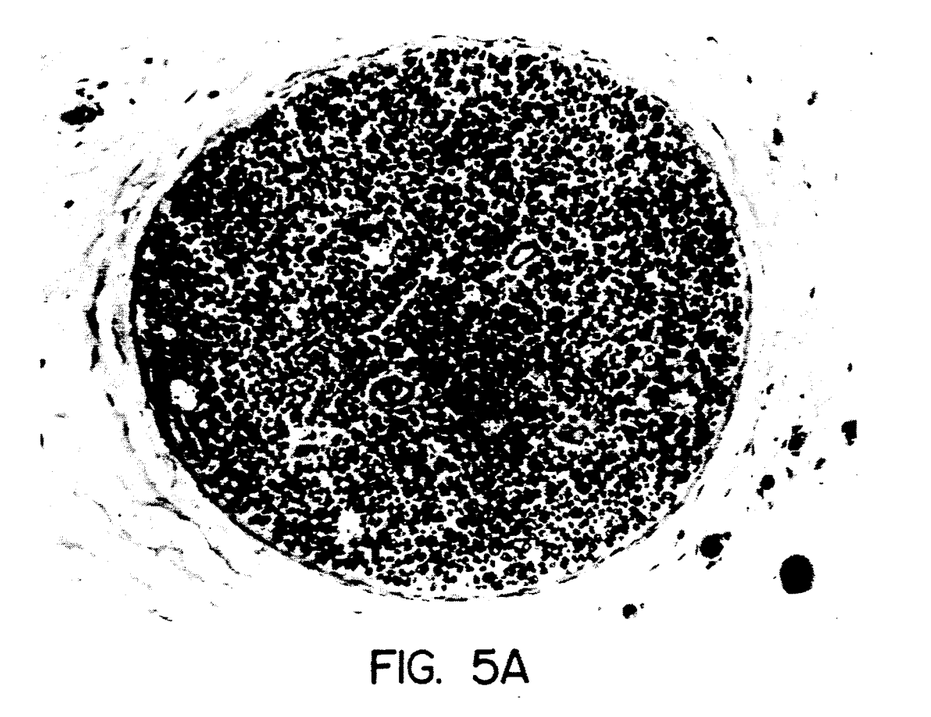
Figure 5B:
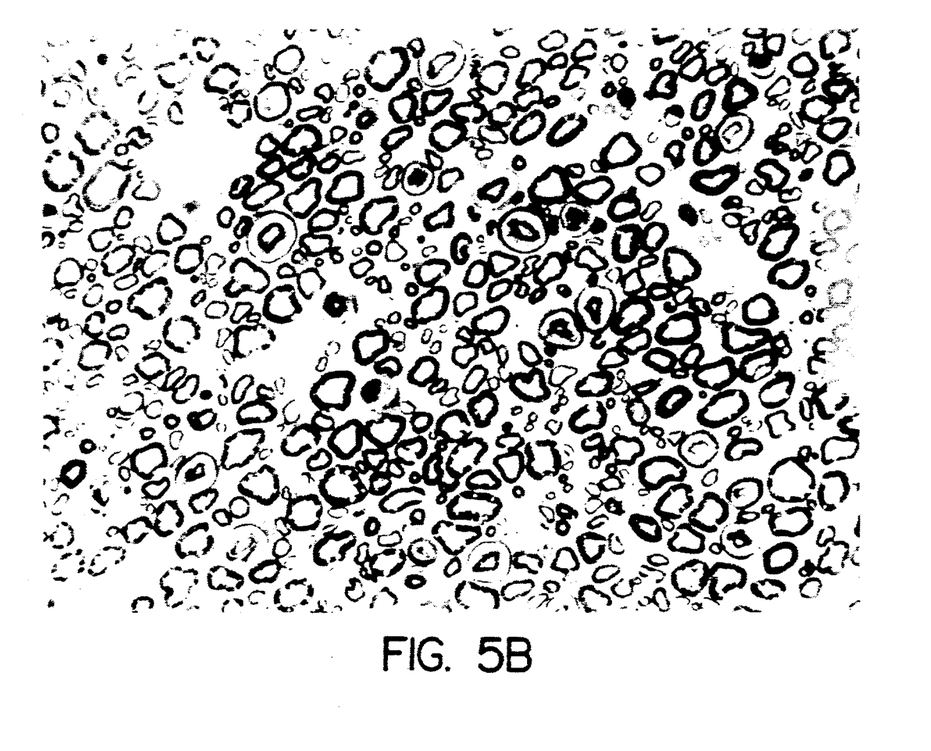
Figure 5C:
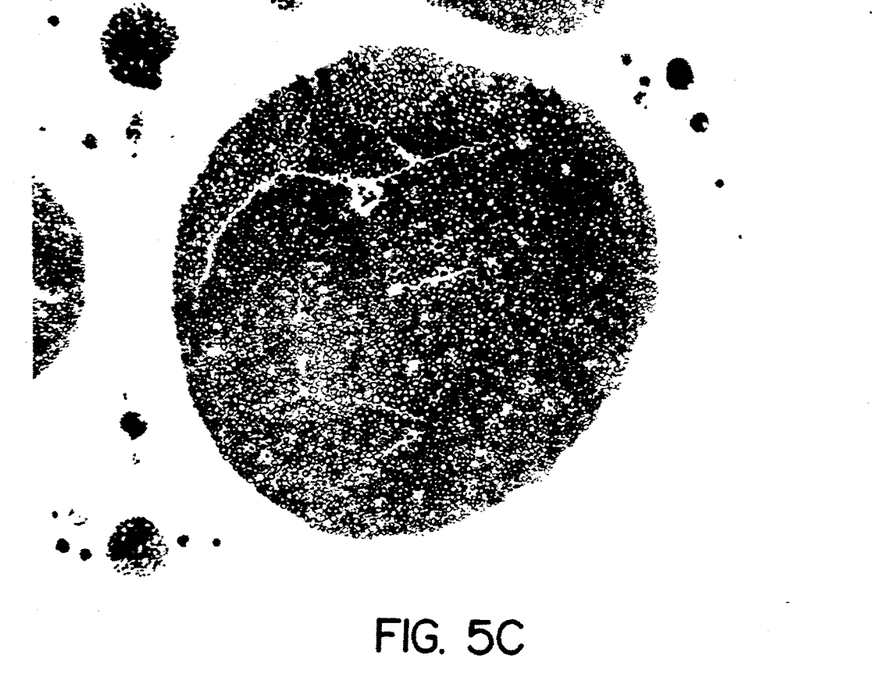
Figure 5D:
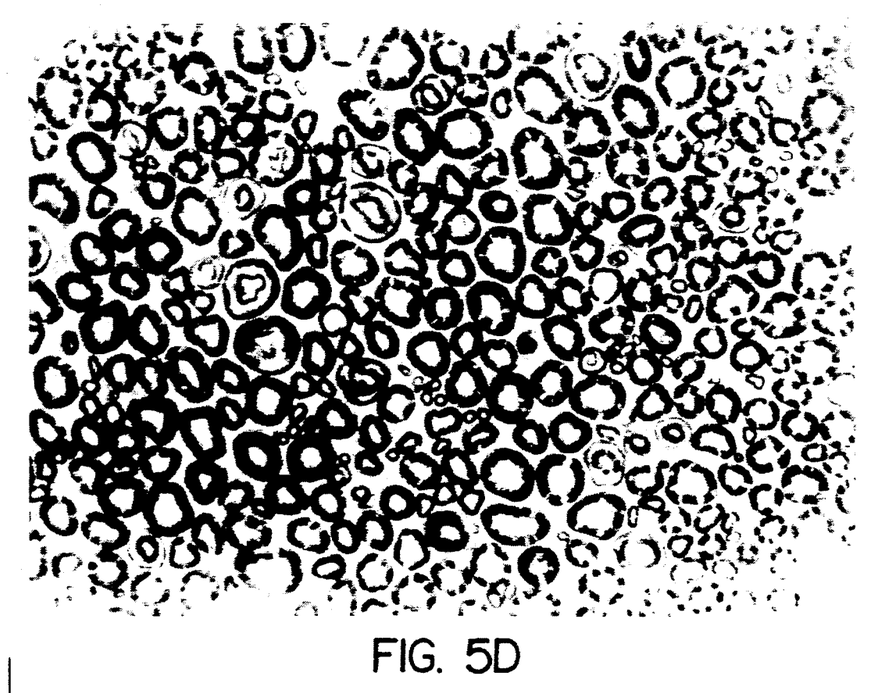
Figure 6:
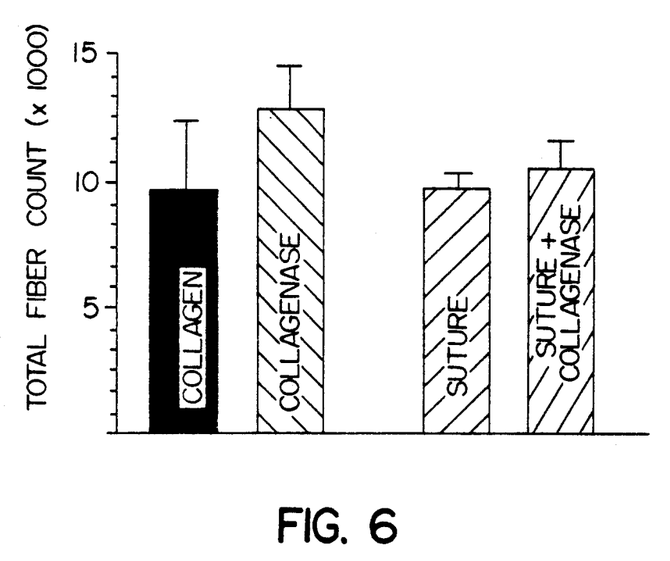

Collagenase (Clostridiopeptidase A) is an enzyme produced from the bacterium *Clostridium hystolyticum*. Highly purified collagenase uniquely cleaves bonds in the collagen structure permitting other enzymes to act on the resulting molecular fragments.

Purified collagenase, used in the following work, is free of detectable caseinase and nonspecific protease activity. It can be obtained from Advance Biofactures Corporation, Lynbrook, N.Y., sold under the trademark "Nucleolysin". The frozen enzyme is thawed and diluted with normal saline solution plus 2 mM calcium chloride to the desired concentration. Enzyme activity, given in ABC units, is determined using an insoluble substrate, undenatured bovine tendon, according to a modification of the method of Mandl et al. (Arch. Biochem. Biophys. 74:465-475, 1958). A unit of activity corresponds to the release of ninhydrin reactive material equivalent to nanomoles leucine equivalents released in one minute from undenatured collagen. The collagenase is obtained from culture of a special strain of *Clostridium histolyticum* and purified by a chromatographic technique.

The following information demonstrates and exemplifies various aspects of the invention.

Materials and Methods

The right sciatic nerve of the rat was used as an experimental model in two series (I=collagenase in the silicone model; II=collagenase in epidural suture with fibrin). A total of 42 rats (male, weight about 300 g) were examined in these series.

The operation was performed at time=0 days under general anesthesia (40-50 mg/kg body weight). The sciatic nerve was visualized through a lateral incision on the right side. Transection of the nerve was effected with a clean cut by microscissors, prior to which 3 marking sutures (9-0. Ethilon) were put in place. The latter were inserted before transection as means of orientation, to obtain like conditions of rotation in all animals.

No immobilization was carried out postoperatively.

Preliminary tests established that the anesthetic used produces no alteration in properties of nerve conduction in the test region. In addition, it was demonstrated that collagenase is not inhibited by either fibrin glue or clot material, and collagenase caused no alteration in nerve conduction properties in the test region.

Effect of Collaqenase on Result of Nerve Regeneration in the Silicone Model (Series I)

In the first part of the study (Series I) the hypothesis was tested in the silicone tube model. The experimental group (Series IB) consisted of 12 animals and the control group (Series IA) likewise of 12 animals.

The two nerve ends were inserted into a silicone tube 5 mm in length (outside diameter 2 mm; inside diameter 1.5 mm—Wehabo, Dusseldorf) which had previously been filled in the center with an average of 1.7 mg collagen (type I bovine collagen—Sigma No. C-9879) in a length of 1 mm, until they struck the collagen mass. The nerve was anchored and secured to the silicone tube by 3 holding sutures (9-0), proximally as well as distally. This was followed by the injection of 0.05 ml collagenase (50 units) through the silicone tube into the center of the collagen.

Complete clinical and neurophysiological examinations were performed preoperatively, on the 7th, 12th, 15th, 19th, 25th, 32nd, 40th, 60th, (80th) and 90th postoperative days in all animals of the two groups. The hind paws were recorded photographically at the same time intervals, to rule out autonomous denervation reactions.

At the end of the observation period, 6 treated nerves each of the experimental group (IB) and of the control group (IA) were processed further for histology and morphometry.

Effect of Collagenase in Epidural Suture Technique Combined with Fibrin Glue (Series II)

Approach and transection of the nerve were carried out in the same way as in Series I. The epidural suture was made with 6×9-0 nonresorbable sutures (Ethilon ®).

Following suture, the suture region was thoroughly coated with a fibrin/collagenase mixture (1 ml of this mixture consisted of: 1000 I.U. aprotinin; 50 I.U. thrombin; 1000 U. collagenase; total mixture applied 0.05 ml 50 U. collagenase). After the region of transection was packed with this mixture, an additional injection of 0.01 ml (=25 U. collagenase) was made into each of the proximal and distal nerve segments in a region of about 1 mm.

The 12 animals of the experimental group were treated identically to the 6 animals of the control group (fibrin glue without collagenase+saline).

Six treated nerves of the experimental group (IIB) and 3 of the control group (IIA) were examined histologically and morphometrically by the same methods as in Series I.

The examination intervals during the 90-day observation period were identical to those of Series I.

Clinical Findings

FIG. I shows the average motor performance of the treated right hind paw in Series I+II evaluated by deMedinaceli's method (SFI=sciatic functional index) 90 days after transection of the right sciatic nerve.—100% corresponds to complete paresis of the hind paw.

Motor performance after 90 days is significantly higher in the experimental group of Series +I.

In Series I, after 90 days, 11 animals (total n−12) of the experimental group exhibited a normal toe spreading reflex, while in the control group this was detectable in only 5 animals (total n=12).

In Series II, the toe-spreading reflex was observed on the right side in 10 animals (total n=12) of the experimental group and in 3 animals of the control group (total n=6).

NEUROPHYSIOLOGIC FINDINGS

Evoked Spinal Potential (SSEP Li)

The SSEP response, in particular the level of amplitude, was regarded as a measure of functioning afferent axons.

At test times t=90 days, the amplitudes of evoked spinal responses showed higher amplitudes in the experimental groups of both series [IIA/B m: 7.33 uV/10.64 uV; s.d.: 3.83/1.63; p<0.162) (IA/B m: 6.408 uV/11.058 uV; s.d. 4.977/2.81; p <0.01)]. Even at time t=60 days, there were differences between experimental and control group in both series, although these were on the order of p <0.024 (Series I) and p<0.023 (Series II) in the t test.

On the 25th postoperative day, an evoked spinal potential was observed in 9 animals (total n=12) of the experimental group IB (IIB: 10 animals; total n=12), while an evoked spinal potential was detectable in 5 animals (total n=12) in the control group of Series I and in 1 animal (total n=6) in Series II.

CMAP (Amplitude of Evoked Muscle Potential)

FIG. II shows the results of the measurement of amplitudes at times t=0 days, t=60 days and t=90 days in both series.

Level of amplitudes was measured in the intrinsic muscles of the foot (in mV) after stimulation of the sciatic nerve proximal to the site of transection of the nerve. Compared with the respective control group, a highly significant increase in amplitude of the total muscle potential is striking in both collagenase-treated series [Group IA/B preop. m: 6.067 mV/5.792 mV; s.d.: 0.794/0.406; 16 degrees of freedom; p<0.338. 90 days m: 0.227 mV/1.408 mV; s.d.: 0.403/0.571; 21 degrees, of freedom; p<0.0001) (Group II/ A/B preop. m: 4.58 mV/4.56 mV; s.d.: 1.3/0.55; 16 degrees of freedom; p<0.954. 60 days m: 0.13 mv/1.07 mV; s.d.: 0.3/0.63; 16 degrees of freedom; p<0.004. 90 days m: 1.52 mV/ 3.37 mV; s.d. 0.44/0.75; 16 degrees of freedom; p<0.0001)]. Means with standard deviation correspond to leads of a total of 42 animals. The highest amplitude values (3.37 mV) at the end of the observation period were obtained by the nerves which were treated with collagenase/-suture+fibrin (Group IIB). These nerves exhibited values close to those prior to the operation (4.56 mV).

SSEP and CMAP of One Animal

FIG. III shows representative potentials in rat No. 42, which was treated with collagenase.

The tracings are of representative leads of evoked spinal potential (SSEP Ll. tracing on left) and of evoked muscle activity in the intrinsic muscles of the foot (CMAP, tracing on right) after stimulation of the sciatic nerve proximally (CMAP) and distally (SSEP) of the site of transection after injection of collagenase in simultaneous epidural suture and fibrin coating. Immediately after transection of the nerve, this animal (No. 42) developed a complete paresis of the foot, which showed clear clinical improvement from the 60th day. The filter setting was LF: 10 Hz+HF: 10 kHz, the SSEP (tracing on the left) corresponds to 64 averaged responses, the CMAP (tracing on the right) corresponds to a single stimulation of the nerve. Supramaximal stimuli were employed. If a threshold value determination was not possible because of complete paresis, we stimulated with 40 V. Note the distinct increase in amplitude in the CMAP on the 60th and 90th post-operative days, which was accompanied by clinical improvement. The clinical and neurophysiological test values of the unoperated opposite side were unremarkable.

Velocity of Motor Nerve Conduction (VNC)

In Series I (silicone model) the VNC was determined preoperatively in all animals. After 90 days a normal muscle potential following stimulation at two different locations of the right sciatic nerve was obtained in all animals of the collagenase group (n=12), while in the control group this was possible in only 4 animals (n=12).

After 60 days this was possible in 10 nerves of the experimental group and in no nerve of the control group.

In Series II (epidural suture with fibrin), the VNC was likewise determined in all animals, if possible.

After 90 days determination of the VNC was possible in all animals of the experimental group (IIB) and in all animals of the control group. However, the experimental group exhibited a distinctly higher VNC (IIB m: 27.42 m/s. s.d.: 4.62; IIA m: 19 m/s. s.d.: 5.29; 16 degrees of freedom; $p<0.003$).

After 60 days determination of the VNC in the operated nerve was possible in all animals of the experimental group and in one animal of the control group (total n=6).

There was no significant difference in preoperative values in the two groups ($p<0.593$).

Thus, compared with all other groups of Series I+II, Group IIB also obtained the highest values in velocity of nerve conduction.

FIG. IV summarizes the means with standard deviation of the velocity of nerve conduction (m/sec) of Groups I+II after 90 days. The animals in which determination of the VNC was not possible because of total loss of potential were not included in the statistical analysis of UNC. The two columns on the left show means with standard deviation in Group I, in which the effect of a total of 50 units of collagenase on regeneration was studied in the silicone model (control/collagenase m: 19 75/24.25 m/s; s.d.: 4.856/6.510; 14 degrees of freedom; $p<0.229$). The two columns on the right show means with standard deviation in Group II, in which the effect of a total of 100 units of collagenase was studied in epidural nerve suture with fibrin glue (controls/collagenase m: 19/27.42 m/s; s.d.: 5.29/4.62; 16 degrees of freedom; $p<0.003$). The distinct difference in the velocity of conduction of motor fibers of Group IIB, compared with Group IIA, is striking.

Morphometric, Findings

FIGS. V(A, B, C+D) shows nerve cross-sections in various magnifications of a nerve which was treated with collagenase in the silicone model (FIGS. V A and B), and of an untreated normal nerve (FIGS. V C and D). (A=30x+B=1000x) Nerve cross-section 5 mm distal to nerve transection after 3 months' regeneration. In the silicone model 50 units of collagenase were injected at time t=0. (C+D) Nerve cross-sections of an untreated normal nerve; note the pronounced homogeneous myelinzation.

FIG. VI shows the total number of myelinized fibers in Series I and II in experimental and control groups. The count was at 5 mm distal to the original site of nerve transection. The bars represent means with standard deviation.

With the use of collagenase in combination with fibrin and suture (Series II), the average count was on the order of 10,476 myelinized nerve fibers (s.d.: 1107); in the control group, it was on the order of 9,685 myelinized fibers (s.d.: 620). In the collagenase group of Series II there was an increased total fiber count at a low level of significance ($p<0.235$).

With the same investigatory technique, a total count of 12,760 fibers (s.d.: 1553) was obtained in the silicone model study, while a total fiber count of 9588 (s.d.: 2728) was found in the control group. The increase in the fiber count was significantly greater ($p<0.047$) in the collagenase group of Series I.

Morphometry in Series I (silicone model) and II (suture+fibrin model), in terms of relative total fiber diameter, and percentage cluster of nerve fibers, in diameter groups ranging from 1.0 to 10 μm in steps of 0.5 μm, revealed no appreciable differences between collagenase-treated and control groups.

CONCENTRATION AND DOSAGES

The invention is useful in the repair of injured nerves of humans and animals. Generally speaking, similar concentrations of collagenase can be used.

Concentrations of about 500 to 1,000 ABC units collagenase per ml are ordinarily satisfactory, although lower or higher concentrations; for example down to 200 u/ml or less and up to 2,500 u/ml or more, may be employed. The collagenase will be used in a pharmaceutically acceptable medium, such as normal saline solution, which may be enhanced with any chosen adjuvant, such as $CaCl_2$ in a concentration of 2 mM.

The dosage, i.e. quantity of collagenase, applied to the affected area will be dependent on the need. For a simple severed peripheral nerve trunk easily sutured, 50 to 100 units will ordinarily be sufficient. The physician will use his judgment in the amount of collagenase used for more extensive repairs.

PHARMACEUTICAL KIT

For convenient use during surgery when fibrin is to be used as adhesive, collagenase and fibrin can be packaged together and sold as a pharmaceutical kit. The kit can contain a mixture of the two components, with collagenase present in a concentration preferably ranging from about 500 to 1,500 units/ml. One suitable formulation is: 1 ml containing 1,000 I.U. aprotinin; 50 I.U. thrombin, 1,000 ABC units collagenase. For greater shelf life, and to provide the surgeon with freedom to choose amounts and concentration, collagenase and fibrin or fibrin precursors can be kept separate in the kit.

In view of the preceding description, further modifications and alternative embodiments of the instant invention will be apparent to those skilled in the art. Accordingly, the preceding descriptions and examples are to be construed as explanatory and illustrative only and are for the purpose of teaching and enabling those skilled in the art to practice this invention. It should be understood that the amount of the collagenase required will vary. Suitable amounts in a given situation can be determined by the physician and the following factors, among others, should be considered: the nature of the nerve trauma being treated, the surgical methods used for repair, the concentration of collagenase in the solution or in the fibrin, the type of collagenase used, the nature of the tissue adjacent to the site of injury being repaired.

While the specific embodiment of the above described invention is to be understood to be the best mode presently contemplated, it is by no means the only embodiment possible. The scope of the invention is defined by the following claims and by any equivalent modifications and variations that fall within the true spirit of the invention.

I claim:

1. An adhesive formulation consisting essentially of fibrin adhesive and collagenase present in an amount and concentration effective to enhance regeneration and rejoining of a severed nerve when said formulation is used as adhesive for the stumps.

2. An adhesive formulation according to claim 1 wherein the collagenase is present in a concentration of about 500 to 1,500 ABC units/ml.

3. A pharmaceutical kit for surgical use consisting essentially fibrin adhesive and collagenase packaged together.

4. A kit according to claim 3 wherein the fibrin adhesive and collagenase are admixed.

5. A kit according to claim 4 wherein the collagenase is present in a concentration of about 500 to 1,500 ABC units/ml.

6. A kit according to claim 3 wherein the fibrin adhesive and the collagenase are not admixed.

* * * * *